(12) United States Patent
Kubacki et al.

(10) Patent No.: US 6,261,520 B1
(45) Date of Patent: Jul. 17, 2001

(54) APPARATUS FOR PREPARING SAMPLES WITH SLIDER BOX

(75) Inventors: Michel Kubacki, Louvres; Eric Marteau D'Autry, Paris, both of (FR)

(73) Assignee: Gilson, S.A. (FR)

( * ) Notice: Subject to any disclaimer, the term of this patent is extended or adjusted under 35 U.S.C. 154(b) by 0 days.

(21) Appl. No.: 09/380,989

(22) PCT Filed: Mar. 12, 1998

(86) PCT No.: PCT/FR98/00506

§ 371 Date: Sep. 13, 1999

§ 102(e) Date: Sep. 13, 1999

(87) PCT Pub. No.: WO98/41875

PCT Pub. Date: Sep. 24, 1998

(30) Foreign Application Priority Data

Mar. 14, 1997 (FR) .................................................. 97 03092

(51) Int. Cl.⁷ .................................................. G01N 30/00
(52) U.S. Cl. .............................. 422/63; 210/282; 422/65; 422/69; 422/70; 422/101; 422/104
(58) Field of Search .................. 422/63, 65, 69, 422/70, 100, 102, 104, 101; 210/282

(56) References Cited

U.S. PATENT DOCUMENTS

| 4,155,711 | * | 5/1979 | Zelagin et al. . |
| 4,766,082 | * | 8/1988 | D'Autry . |
| 5,260,028 | * | 11/1993 | Astle . |
| 5,413,708 | * | 5/1995 | Huse et al. . |
| 5,417,123 | * | 5/1995 | D'Autry . |
| 5,585,068 | * | 12/1996 | Panetz et al. . |
| 5,585,070 | * | 12/1996 | Lessard et al. . |

FOREIGN PATENT DOCUMENTS

| 4230719 A1 | * | 3/1994 | (DE) . |
| 0527562 A2 | * | 2/1993 | (EP) . |

* cited by examiner

*Primary Examiner*—Jan Ludlow
(74) *Attorney, Agent, or Firm*—Mason, Kolehmainen, Rathburn & Wyss

(57) ABSTRACT

The invention concerns an apparatus for preparing samples for analysis having at least a liquid-injecting needle (6), at least a column (32) for receiving the injecting needle, at least a tube (48), device (6, 26) for the tube and the column relative horizontal displacement between a position of coincidence in which the column bottom aperture (36) extends above the tube top aperture (50), and a relative lateral offset position of the two apertures (36, 50), and adapted device (6, 60) for the tube (48) and the column (32) relative vertical displacement such that in position of coincidence, the apertures (36, 50) interpenetrate, including vertical guide device for either the tube (48) or the column (32). The vertical guide device is adapted to operate the guiding under horizontal loading effect.

11 Claims, 3 Drawing Sheets

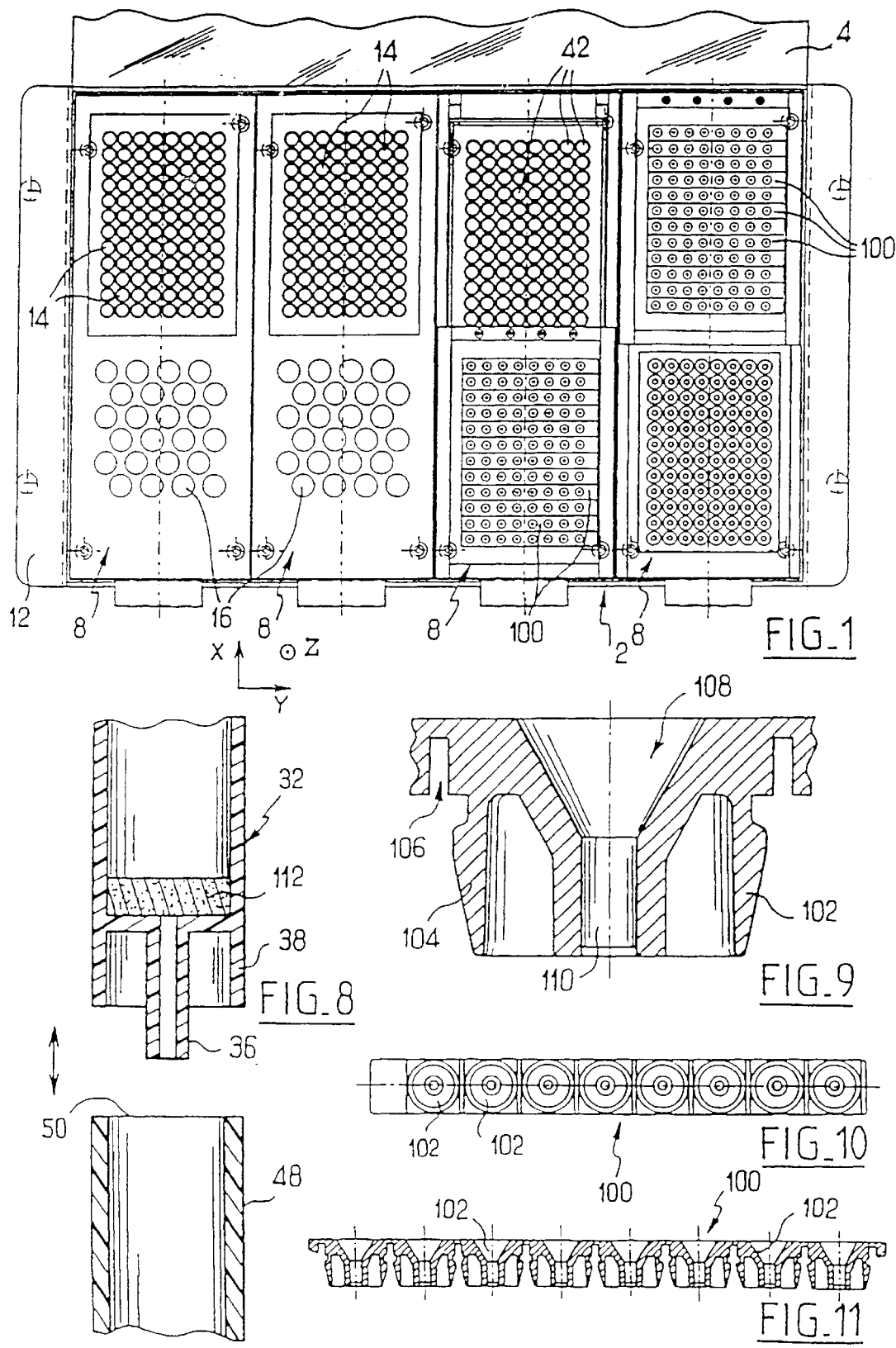

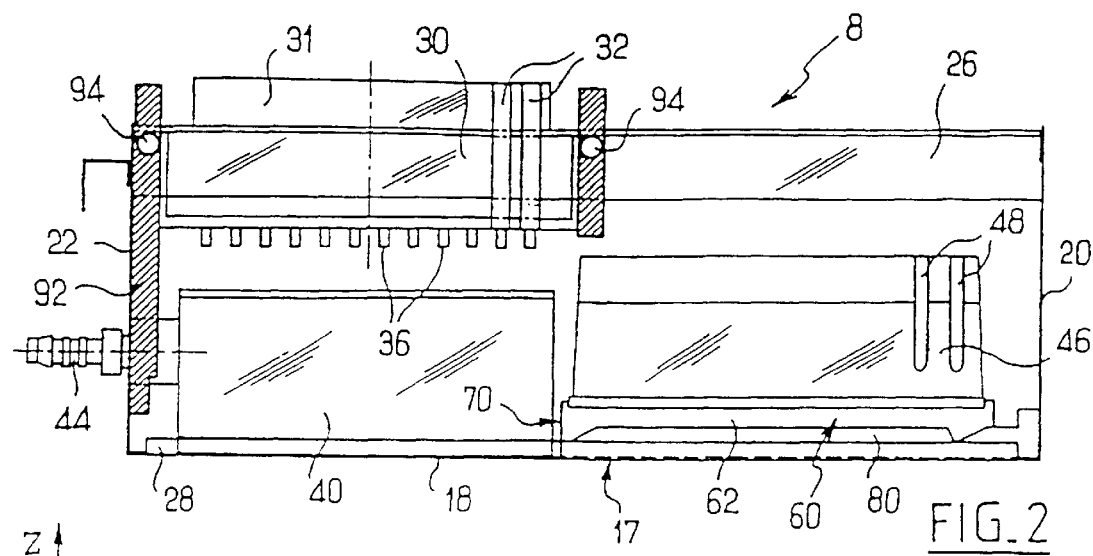
FIG_2
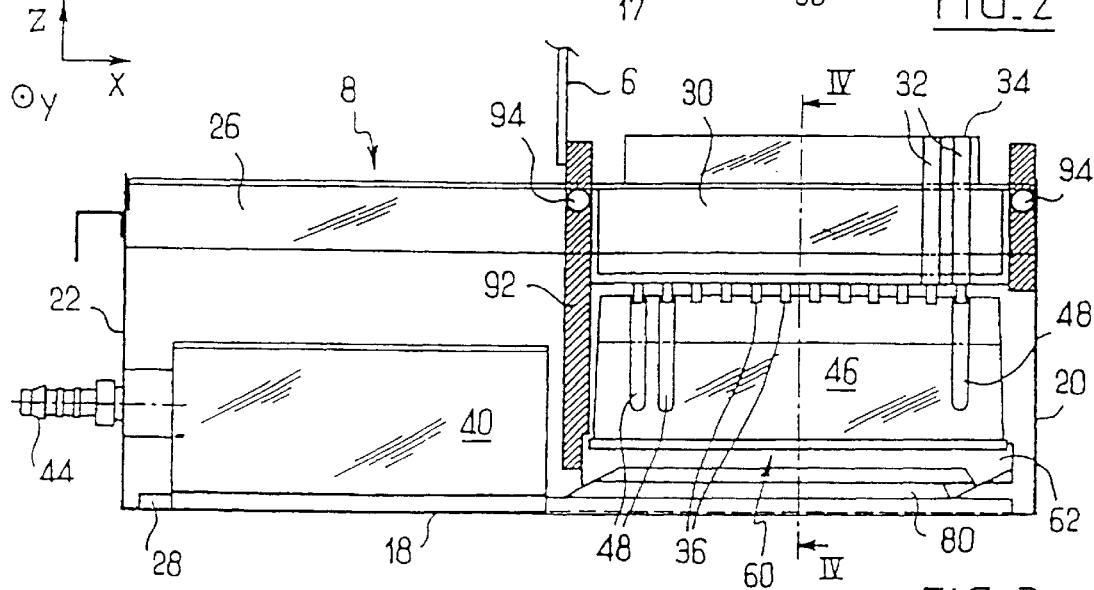
FIG_3
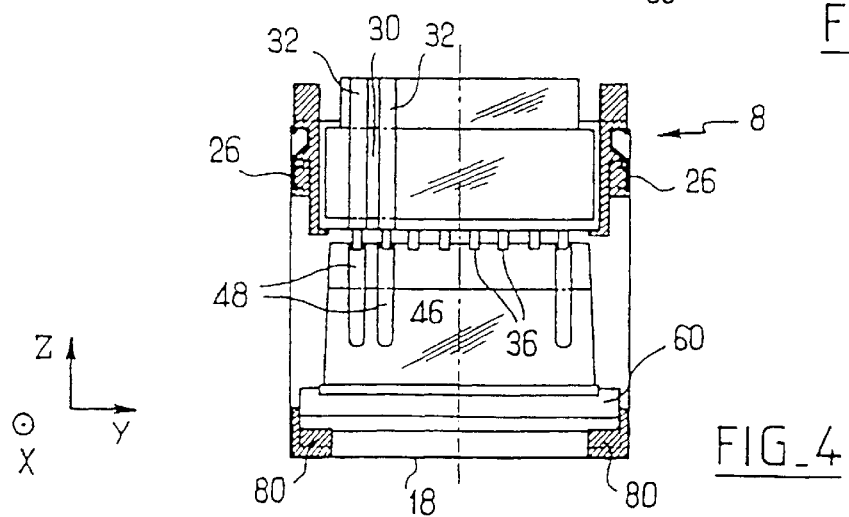
FIG_4

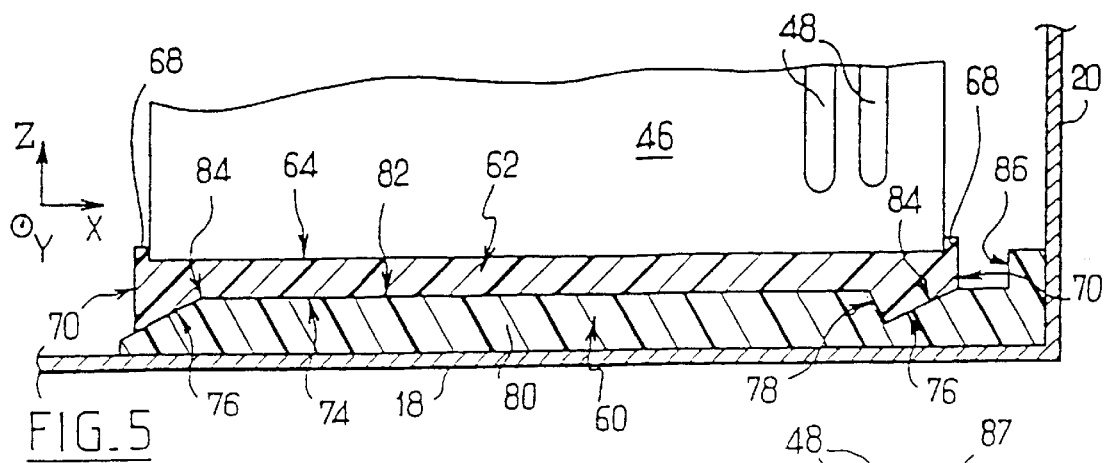
FIG_5
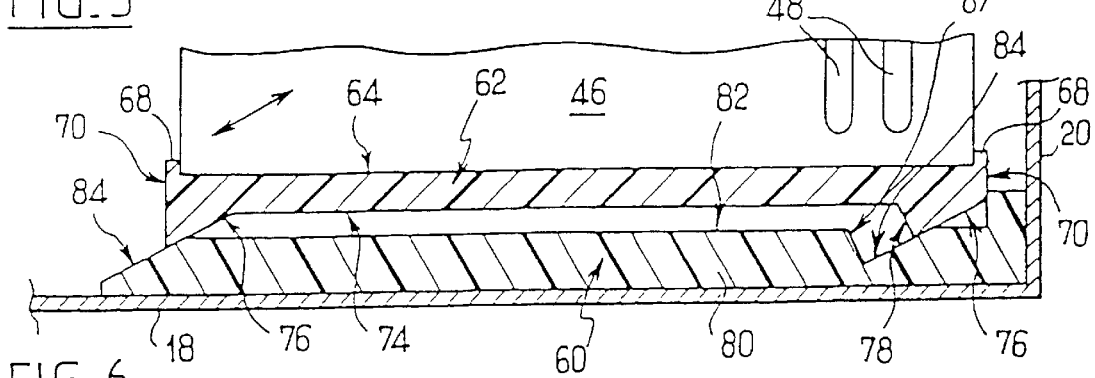
FIG_6
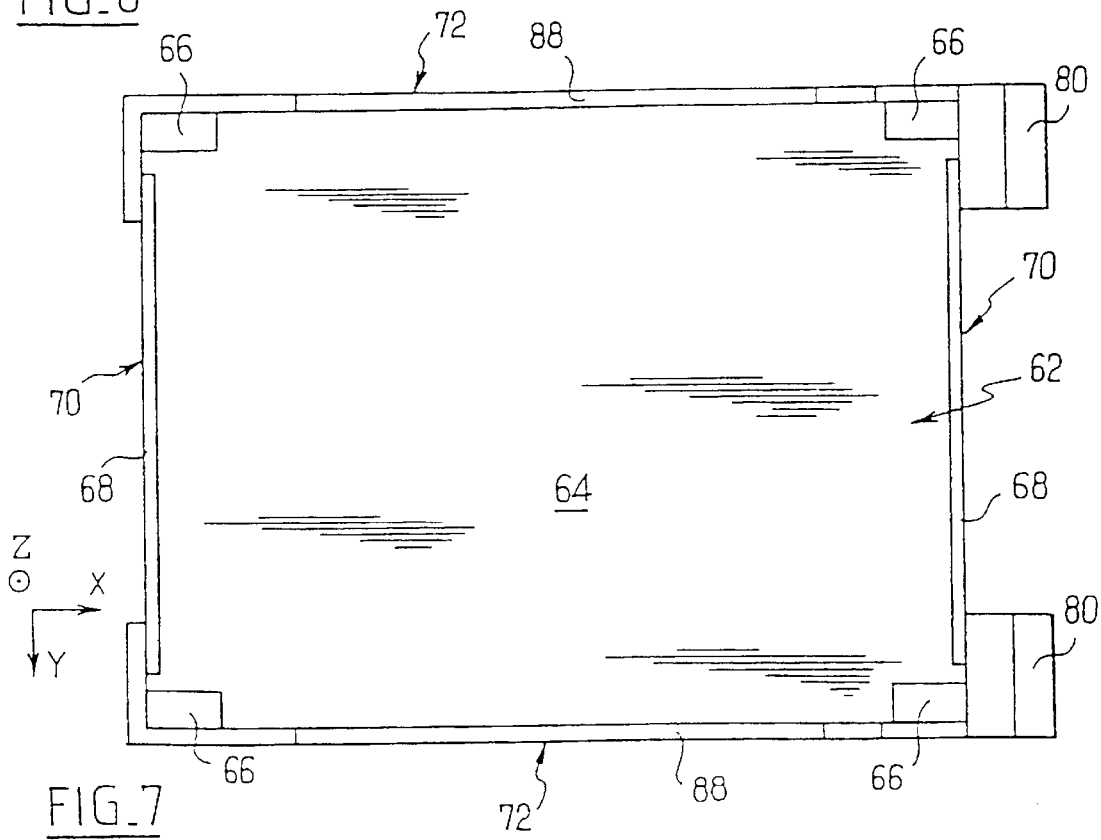
FIG_7

APPARATUS FOR PREPARING SAMPLES WITH SLIDER BOX

BACKGROUND OF THE INVENTION

The invention relates to apparatus for preparing samples for analysis, for example for analysis by chromatography.

1. Field of the Invention

Document EP-0 180 511-B1 discloses an apparatus of this type, comprising a baseplate, a set of columns running across the upper part of the baseplate and each receiving an agent in powder form, and a set of tubes spread out in a carriage, toward the lower part of the baseplate. The carriage can move in sliding between a position of coincidence in which an aperture at the bottom of the columns is opposite an aperture at the top of the tubes so that liquid can be transferred from the columns into the tubes, and a laterally offset position in which the columns are placed over a basin borne by the carriage and able to receive the content of the columns. The apparatus comprises a mobile injection needle designed to inject various liquids into the aperture at the top of the columns that they pass through the agent in powder form and are collected in the tubes. An apparatus of this kind makes it possible, starting from raw samples, to prepare in the tubes, in an automated fashion, a great many samples designed for subsequent analysis by chromatography, or any other kind of analysis, such as mass spectrography and radioimmunoassay.

2. Background of the Invention

However, a drawback of this apparatus is that when the columns and tubes are in the position of coincidence, there is a risk that the liquid transferred from each column will splash toward the tubes adjacent to the tube associated with the column in question. There is therefore a risk of these adjacent tubes becoming contaminated. Such a risk reduces the reliability of the subsequent analysis of the samples. This drawback is particularly keenly felt when the aperture at the bottom of the columns consists of a small nozzle and the liquid is driven through the nozzle under pressure. In such an instance, the risk of splashing toward the adjacent tubes is very high.

There is therefore a desire to have an apparatus which exhibits the same advantages but in which the risk of cross-contamination of samples is considerably reduced.

Document U.S. Pat. No. 5,260,028 discloses an apparatus for solid-phase extraction, comprising a motor for driving the horizontal movement of the tubes with respect to cassettes along horizontal slideways, and another motor for driving the tubes in a vertical movement with respect to the cassettes along vertical slideways with a view to coupling them so that liquid can be transferred from one to the other without splashing. However, this apparatus is of a complicated and bulky structure.

One purpose of the invention is to provide an apparatus of a different type, and which in particular is of simpler and less bulky design.

SUMMARY OF THE INVENTION

In order to achieve this aim, the invention provides an apparatus for preparing samples for analysis, comprising at least one liquid-injecting needle, at least one column designed to take the injection needle, at least one tube, means for the horizontal relative movement of the tube and of the column between a position of coincidence in which an aperture at the bottom of the column lies over an aperture at the top of the tube, and a position in which the two apertures are offset laterally relative to each other, and means for the relative vertical movement of the tube and of the column which are designed so that, in the position of coincidence, the apertures interpenetrate, these means comprising means for vertically guiding either the tube or the column, the vertical-guidance means being designed to provide guidance under the effect of a horizontal force.

Thus, in the penetration position, splashes are arrested by the walls of the tube and/or of the column, and do not contaminate the adjacent samples. The reliability of the subsequent analysis is therefore preserved. What is more, the drive means which produce the vertical movement may be the same as those which produce the horizontal movement. The apparatus can therefore have a simpler and less bulky structure.

Advantageously, the apparatus comprises means for horizontally forcing either the tube or the column, the guide means being independent of the forcing means and designed to provide vertical guidance under the effect of the horizontal force applied by the forcing means.

Thus, all that is required is for the vertical-guidance means to be located in the vicinity of the tube or of the column, it being possible for these means to be somewhat compact.

Advantageously, the forcing means comprise at least one arm designed to apply force to either the tube or the column, and secured to the other one, column or tube.

Thus, as the column and the tube move closer toward the position of coincidence, this initiates and automatically brings about the interpenetration of the apertures, without separate specific control means being needed to effect this.

Advantageously, the guide means comprise at least one ramp and a bearing piece designed to be moved with respect to the ramp, in contact with this ramp, in order to provide guidance.

Advantageously, the ramp and that zone of the bearing piece which is designed to be in contact with the ramp, are made of polyethylene terephthalate or polyoxymethylene.

Thus, the bearing piece slides well against the ramp. Furthermore, this material is chemically inert.

Advantageously, the apparatus comprises means for holding the column and the tube in the position of coincidence with the apertures interpenetrating.

Thus, any inadvertent change in the relative position of the tube and of the column in the position of coincidence is avoided, particularly when liquid is being transferred. If this were not the case, such a change could occur, for example, under the effect of vibrations and/or of gravity when the vertical movement involved raising the tube toward the column.

Advantageously, the holding means comprise magnetic means.

Advantageously, the apparatus comprises a film which covers the aperture of the tube. This film can be perforated by a nipple on the column so as to create an unsealed joint. The optional presence of such a film makes it possible to limit the ventilation of the zone in question and any possible resulting evaporation.

Advantageously, the apparatus comprises a baseplate, the column extending to a set horizontal level with respect to the baseplate, the vertical-movement means being designed to move the tube with respect to the column.

Advantageously, the column can move with horizontal sliding with respect to the baseplate.

The invention also provides for a carrier designed to form part, particularly such that it is removable, of an apparatus for preparing samples for analysis, the carrier comprising at least one column, at least one tube, means for the relative horizontal guidance of the tube and of the column between a position of coincidence in which an aperture at the bottom of the column lies over an aperture at the top of the tube, and a position in which the two apertures are laterally offset relative to each other, the carrier comprising means for the relative vertical guidance of the tube and of the column, which are designed so that, in the position of coincidence, the apertures interpenetrate, the guide means being designed to provide vertical guidance under the effect of a horizontal force applied to the tube or to the column.

A carrier of this kind may form part, for example in number, of an apparatus according to the invention.

BRIEF DESCRIPTION OF THE DRAWINGS

Other features and advantages of the invention will become clearly apparent from the following description of a preferred embodiment which is given by way of non limiting example. In the appended drawings:

FIG. 1 is a partial plan view of an apparatus according to the invention;

FIG. 2 is a side view of one of the carriers of the apparatus of FIG. 1, in the offset position;

FIG. 3 is a view similar to FIG. 2, showing the carrier in the position of coincidence;

FIG. 4 is a view in cross section on the plane IV—IV of the carrier of FIG. 3;

FIG. 5 is a part view in longitudinal section on a larger scale, of a detail of the carrier, showing the plate in the lowered position;

FIG. 6 is a view similar to FIG. 5 showing the plate in the raised position;

FIG. 7 is a plan view of the plate on the two slideways;

FIG. 8 is a part view in axial section in the region of the aperture at the bottom of a column and of the aperture at the top of a tube;

FIG. 9 is a part view in axial section of a stopper of a strip of stoppers;

FIG. 10 is a plan view of the strip of FIG. 9; and

FIG. 11 is a view in longitudinal section of the strip of FIG. 9.

DETAILED DESCRIPTION OF THE PREFERRED EMBODIMENT

In the preferred embodiment which will now be described, the apparatus 2 for preparing samples for analysis is, in principle, of the type described in document EP-0 180 511-B1. In particular, its structure and operation are similar.

The apparatus comprises a fixed casing 4 containing, in particular, the control electronics. It comprises at least one vertical needle 6 (see FIG. 3) connected to means designed to cause the needle to draw in and inject fluids such as air or various liquids. The needle 6 is connected to the casing 4 with a known mechanism, not depicted, allowing the needle to move freely with respect to the casing in the three directions X, Y and Z, namely the longitudinal, transverse and vertical directions.

The apparatus comprises carriers 8, in this particular instance 4 of these, with the overall shape of a rectangular parallelepiped and placed removably side by side with their longitudinal sides facing each other, on a plate 12 of the apparatus 2 so that they are contiguous with the baseplate 4 and within reach of the needle 6.

The two carriers 8 furthest to the left in FIG. 1 carry vertical columns 14, 16 which may, for example, be tubes or cavities, respectively containing raw samples to be prepared and reagents used for this preparation.

One of the two right-hand carriers 8, which are identical to each other, will now be described in detail with reference to FIGS. 2 to 4.

The carrier 8 comprises a baseplate 17 with a horizontal flat bottom 18 and two vertical flat walls 20 at the front and 22 at the rear, which are mutually parallel and rise up from the longitudinal ends of the bottom 18. The baseplate 17 comprises two mutually parallel horizontal profiled rails 26 which are parallel to the longitudinal direction X of the bottom 18 and extend from the front wall 20 to the rear wall 22, at the upper ends thereof. The baseplate 17 also has two longitudinal rims 28, parallel to the rails 26, running vertically and projecting out from the longitudinal edges of the bottom 18. The aforementioned elements of the carrier are, in this instance, made of a rustproof ferromagnetic metal, such as a stainless steel.

The carrier 8 comprises a carriage 30 supported by the two rails 26 in such a way that it can move with longitudinal sliding with respect to the baseplate 17, along the rails, from the front wall 20 to the rear wall 22. The carriage 30 has longitudinal slots collaborating with the profile of the rails 26 such that any relative vertical movement of the carriage 30 and of the rails 26 upward or downward is impossible. Thus, the carriage 30 is fixed permanently to the rails. At its center, the carriage has a vertical through-hole which houses a block 31 made of plastic in the shape of a rectangular parallelepiped, defining a rectangular array of 8×12 vertical columns 32 of circular cross section. Each column 32 has a circular aperture 34 at the top and a narrowed nozzle-shaped aperture 36 at the bottom, surrounded by a cylindrical surround 38 which does not extend down as far as does the nozzle 36.

The carrier 8 comprises a drainage unit or basin 40, also in the shape of a rectangular parallelepiped, fixed to the bottom 18 near the rear wall 22. This unit defines a rectangular array of 8×12 vertical ducts 42 open at the upper face of the block, and connected within the block to a common discharge pipe communicating with an extension 44 passing through the rear wall 22 of the carrier.

The carrier 8 comprises a block 46 with tubes 48 made of plastic defining a rectangular array of 8×12 vertical tubes 48 of circular cross section the same size as the columns 32. Each tube 48 has a circular aperture 50 at the top which is the same size as the surround 38 at the bottom of the columns and which are open at the upper face of the block 46. The tubes 48 are plugged at their other end so that the tubes can be emptied only via the aperture 50 at the top. The tube block 46 is supported by a raising/lowering unit 60 which will now be described with reference to FIGS. 5 to 7.

The raising/lowering unit 60 comprises a plate 62 of flat rectangular overall shape. This plate has a flat top face 64 equipped, at its four corners, with four respective blocks 66 and, at its longitudinal end edges, with a rim 68, the blocks 66 and the rims 68 extending vertically upward and projecting from the face 64. The blocks 66 and the rims 68 hold the tube block 46 housed on the upper face 64 of the plate 62 in place in the horizontal directions X and Y. The plate has two longitudinal end faces 70 and two side faces 72, all four of which faces are flat and vertical. It has a flat underside 74 parallel to the top face 64.

The plate 62 has two flat ramps 76 which are mutually parallel and inclined with respect to the longitudinal direction X and vertical direction Z. These inclined ramps 76 extend from the longitudinal end faces 70 of the plate. The plate is arranged in the carrier in such a way that the rear ramp 76 is contiguous with the underside 74, and the front ramp 76 is connected to the underside 74 by a flat mating ramp 78, which is also inclined with respect to the directions X and Z.

The raising/lowering unit 60 also comprises two mutually parallel elongate slideways 80 which are axially symmetrical with one another, fixed to the bottom 18 of the baseplate along its longitudinal edges, and distant from one another.

Each slideway 80 has a flat top face 82 parallel to the bottom 18 and the same length as the underside 74 of the plate. Each slideway has two flat ramps 84 which are mutually parallel and inclined with respect to the directions X and Z so as to be parallel to the ramps 76 of the plate. The spacing between the two ramps 84 of one same slideway 80 is equal to that of the two ramps 76 of the plate. Each slideway has a mating ramp 87 adjacent to the front ramp 84, parallel to the mating ramp 78 of the plate and the same size as the latter ramp.

Each slideway 80 near its front end has a flat vertical stop face 86 oriented toward the rear of the carrier. Each slideway 80 has an outer longitudinal rim 88 extending upward at its outer edge, projecting from its top face 82. The two rims 88 provide sliding guidance in the longitudinal direction X of the plate 62 with respect to the slideways 80.

The plate 62 is housed and placed on the slideways 80. It can move in sliding with respect to the slideways between a lowered position depicted in FIG. 5, where the underside 74 of the plate rests on the top face 82 of the slideways, and in which the mating ramp 78 of the plate rests on the mating ramps 87 of the slideways; and a raised position, in FIG. 6, in which the plate 62 is raised further relative to the slideways 80, the aforementioned associated faces being parallel and distant from each other. The change from one of these positions into the other is brought about by sliding (translational movement) of the plate 62 with respect to the slideways 80 in a direction which is inclined with respect to the directions X and Z, by the sliding and the bearing of the ramps 76 of the plate against the ramps 84 of the slideways. The stop face 86 limits the forward sliding of the plate, thereby defining the raised position. The movement of the plate between the two positions is, in this instance, rectilinear, given the shape of the ramps.

The raising/lowering unit 60 is configured in such a way that, with the plate in the lowered position, when the carriage 30 is over the tube block 46, the apertures 50 at the top of the tubes 48 are each opposite and some distance from the apertures 36 at the bottom of the columns 32, in coincidence, coaxial therewith, without interpenetration of the apertures. Furthermore, in the raised position, the aperture 36 at the bottom of the columns, still coaxially in coincidence with the tubes, extends into the aperture 50 at the top of the respective tubes, the tubes being brought closer to the columns upward. The aperture 50 at the top of the tubes is then in contact with the surround 38 of the columns. As an option, it is possible to insert, between the apertures 50 at the top of the tubes and the surrounds 38 of the columns, a film which covers said apertures and can be perforated by the nipples of the columns to provide an unsealed connection to allow the liquid to drop from the column into the tube. This film may be pre-perforated, for example with a cross-shaped preform.

The carriage 30 has two vertical elongate arms 92 extending from a rear end of the carriage downward as far as the level of the plate 62. These arms 92 are designed to come into contact with the rear end face 70 of the plate, so that when the carriage 30 is moved using one or more needles 6 toward the front wall 20 and comes close to this wall, the arms 92 come to bear against the rear face 70 of the plate which initially is in the lowered position. This bearing effect forces the plate 62 horizontally forward, and this causes it to slide from the lowered position (FIG. 5) into the raised position (FIG. 6) in the way mentioned earlier. When the carriage 30 is moved back toward the rear wall 22, the action of gravity on the plate 62 causes the plate to slide the other way, downward, into the lowered position.

The carriage 30 comprises longitudinal permanent magnets 94 housed in the front and rear longitudinal end edges of the carriage. When the carriage is in contact via its front edge with the front wall 20 of the baseplate, the front magnet 94 magnetically cooperates with the metallic front wall 20 to hold the carriage 30 in this position, particularly against the action of gravity exerted on the plate 62 in the raised position. A similar cooperation occurs between the rear wall 22 of the baseplate and the magnet in the rear edge of the carriage 30 to hold the carriage over the basin.

The carriage 30, the plate 62 and the slideways 80 have at least their outer faces made of polyethylene terephthalate and will advantageously be completely made of this material.

The apparatus operates as follows, with respect to these features. The carriage 30 at the start is, for example, in the position of FIG. 2 over the basin 40. This position is the position of the fourth carriage in FIG. 1, counting from the left. In this position, the respective tubes 48 and columns 32 are laterally offset from one another. The needle 6 comes to bear against the rear edge of the carriage 30 and forces it horizontally toward the front wall 20. The needle may just as well come to bear against the front edge or alternatively move the carriage by inserting itself in a well designed for this purpose. The rails 86 then guide the carriage horizontally as far as this wall. When the carriage comes close to this wall 20, the arms 92 come to bear against the rear face 70 of the plate 62, initially in the lowered position, and cause it to rise into the raised position in an inclined rectilinear path guided by the rims 98 and the ramps 76, 84. The tubes 48 are thus raised as far as the columns 32 so that the nozzles 36 enter the tubes. The tubes 48 and the columns 32 find themselves respectively in a position of mutual axial coincidence as soon as the arms 92 come into contact with the plate, and remain thus throughout the travel of the plate between the raised position and the lowered position.

The front magnet 94 cooperating with the front wall 20 holds the assembly in this position after the needle 6 has stopped acting on the carriage. This position of the carriage 30 and of the plate 62 is visible in FIG. 6 and in the case of the fourth carrier 8 of FIG. 1, counting from the left. The needle 6 can therefore enter the aperture at the top of a column 32 sealed hermetically by a stopper 102, for example to inject a fluid and raise the pressure in the column 32 so that liquid can be transferred from the column into the tube via the nozzle 36.

To return the carriage 30 to the initial position, offset toward the rear of the carrier, the needle 6 forces the front edge of the carriage 30 horizontally backward against the magnetic retaining force of the magnet 94, to cause the carriage and the plate to move in the opposite direction. The needle 6 may also come to bear against the front edge or alternatively move the carriage by inserting itself in a well designed for this purpose.

With reference to FIGS. 9 to 11, the hermetic sealing of the aperture 34 at the top of the columns 32 may advantageously be achieved by means of a longitudinal strip 100 of several stoppers 102, for example eight stoppers, connected together. The strips 100 are fixed parallel to each other on the block 31 to plug the apertures 34 at the top of the columns, as shown in FIG. 1. Each stopper 102 has a circular internal lip 104 designed to press against the internal face of the column 32 and a peripheral groove 106 designed to hug the top aperture 34. The internal lip 104 may also be square or of any other geometry that suits that of the column 32. The upper face of the stopper is shaped into a funnel 108, narrowing toward the bottom until it becomes a duct 110, the diameter of which is smaller than that of the needle. The funnel 108 guides the needle 6 as far as the duct 110 which the needle enters so that, with the stopper 102, it seals the column 32 closed. The needle 6 can then inject a liquid or pressurized air into the column so as to force all of the contents of the column to pass through an agent 112 in powder form deposited at the base of the column. Advantageously, this agent in powder form may be replaced by-a pellet cut from a film.

Of course, numerous modifications may be made to the invention without departing from its scope. The invention may be adapted so that the columns 32 are moved vertically with respect to the baseplate 17. The path of the tubes 48 may be other than rectilinear, for example may be circular. This path may also be not inclined, but purely vertical.

The raising/lowering unit 60 may consist of a plate connected to the baseplate by link rods which define deformable parallelograms. The vertical-movement means may have their own drive means independent of the needle 6. The holding means may be disengageable mechanical means.

The vertical-guidance means may comprise just one ramp in contact with a bearing piece.

The needle may be replaced by a raft of several mutually parallel needles which can enter columns simultaneously.

The ramp and that zone of the bearing piece which is designed to be in contact with the ramp may be made of polyoxymethylene.

What is claimed and desired to be secured by Letters Patent of the United States is:

1. Apparatus for preparing samples for analysis, comprising at least one liquid-injecting needle, at least one column designed to receive the injection needle, at least one tube, means for the horizontal relative movement of the tube and of the column between a position of coincidence in which an aperture at the bottom of the column lies over an aperture at the top of the tube, and a position in which the two apertures are offset laterally relative to each other, and means for the relative vertical movement of the tube and of the column which are designed so that, in the position of coincidence, the apertures interpenetrate, the means for the relative vertical movement comprising means for vertically guiding either the tube or the column, characterized in that the means for vertically guiding are designed to provide guidance under the effect of a horizontal force.

2. Apparatus according to claim 1, further comprising means for horizontally forcing either the tube or the column, the means for vertically guiding being independent of the means for horizontally forcing and designed to provide vertical guidance under the effect of the horizontal force applied by the forcing means.

3. Apparatus according to claim 2, characterized in that the means for horizontally forcing comprise at least one arm designed to apply force to either a tube holder or a column holder, and secured to the column holder or tube holder, respectively.

4. Apparatus according to claim 1, characterized in that the means for vertically guiding comprise at least one ramp and a bearing piece designed to be moved with respect to the ramp, in contact with the ramp, in order to provide guidance.

5. Apparatus according to claim 4, characterized in that the ramp and a zone of the bearing piece which is designed to be in contact with the ramp, are made of polyoxymethylene or polyethylene terephthalate.

6. Apparatus according to claim 1, further comprising means for holding the column and the tube in the position of coincidence with the apertures interpenetrating.

7. Apparatus according to claim 6, characterized in that the means for holding comprise magnetic means.

8. Apparatus according to claim 1, further comprising a film which is placed over the aperture of the tube and which can be perforated by the corresponding column without creating a sealed joint.

9. Apparatus according to claim 1, further comprising a baseplate, the column extending to a set horizontal level with respect to the baseplate, the means for the relative vertical movement being designed to move the tube with respect to the column.

10. Apparatus according to claim 9, wherein the column is mounted so as to provide horizontal sliding with respect to the baseplate.

11. Carrier designed to form part of an apparatus for preparing samples for analysis, the carrier comprising at least one column, at least one tube, means for the relative horizontal guidance of the tube and of the column between a position of coincidence in which an aperture at the bottom of the column lies over an aperture at the top of the tube, and a position in which the two apertures are laterally offset relative to each other, further comprising means for the relative vertical guidance of the tube and of the column, which are designed so that, in the position of coincidence, the apertures interpenetrate, the means for relative vertical guidance being designed to provide vertical guidance under the effect of a horizontal force applied to the tube or to the column.

* * * * *